(12) United States Patent
Robinson et al.

(10) Patent No.: US 8,431,397 B2
(45) Date of Patent: Apr. 30, 2013

(54) DIFFERENTIATION OF HUMAN MESENCHYMAL STEM CELLS TO CARDIAC PROGENITOR CELLS THAT PROMOTE CARDIAC REPAIR

(75) Inventors: Richard B Robinson, Cresskill, NJ (US); Michael R Rosen, New York, NY (US); Ira S. Cohen, Stony Brook, NY (US); Peter R. Brink, Setauket, NY (US); Glenn Gaudette, Holden, MA (US); Irina Potapova, Stony Brook, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 546 days.

(21) Appl. No.: 11/227,533

(22) Filed: Sep. 14, 2005

(65) Prior Publication Data

US 2006/0198829 A1 Sep. 7, 2006

Related U.S. Application Data

(60) Provisional application No. 60/609,743, filed on Sep. 14, 2004.

(51) Int. Cl.
*C12N 5/00* (2006.01)
*A01N 63/00* (2006.01)

(52) U.S. Cl.
USPC ............................................ 435/377; 424/1.1

(58) Field of Classification Search .................. None
See application file for complete search history.

(56) References Cited

U.S. PATENT DOCUMENTS

| | | | |
|---|---|---|---|
| 6,007,993 A | 12/1999 | Wobus et al. | |
| 6,261,549 B1 * | 7/2001 | Fernandez et al. | 424/85.1 |
| 6,534,052 B1 * | 3/2003 | Xiao et al. | 424/93.2 |
| 2002/0022259 A1 | 2/2002 | Lee et al. | |
| 2002/0076400 A1 | 6/2002 | Katz et al. | |
| 2005/0186182 A1 * | 8/2005 | Deisher et al. | 424/93.7 |

FOREIGN PATENT DOCUMENTS

| WO | WO 02/083864 | * 10/2002 |
|---|---|---|
| WO | WO-2006/032054 A2 | 3/2006 |

OTHER PUBLICATIONS

Cheng et al., J. Huazhong Univ. Sci. Technolog. Med. Sci., 2003, 23: 154-157, Abstract.*
Kellar et al., Circulation, 2001, 104: 2063-2068.*
Yoo et al., The Journal of Bone and Joint Surgery, 1998, 80: 1745-1757.*
Fukuda et al., Bone Marrow Transplantation, 2003, 32: S25-S27.*
Jiang et al., Nature, 2002, 418: 41-49.*
Lee et al., Blood, on line Oct. 23, 2003, 103: 1669-1675.*
Li et al., Derwent 2011-E23099.*
Xaymardan et al., Stem Cells, 2009, 27: 1911-1920.*
International Search Report and Written Opinion for corresponding Intenational application No. PCT/US05/33422 dated Jun. 18, 2008, pp. 1-4.

* cited by examiner

*Primary Examiner* — Ileana Popa
(74) *Attorney, Agent, or Firm* — Evans & Molinelli PLLC; Judith A. Evans

(57) ABSTRACT

A method for treating a subject afflicted with a cardiac disorder, in vivo, comprises (i) inducing differentiation of a progenitor cell, in vitro, to a cardiogenic cell; and (ii) administering a therapeutically effective amount of the cardiogenic cell of step (i) to the subject, thereby treating the cardiac disorder in the subject. This invention further provides related articles of manufacture and methods.

10 Claims, 4 Drawing Sheets

DIFFERENTIATION OF HUMAN MESENCHYMAL STEM CELLS TO CARDIAC PROGENITOR CELLS THAT PROMOTE CARDIAC REPAIR

This application claims the benefit of U.S. Provisional Application No. 60/609,743, filed Sep. 14, 2004, the contents of which are hereby incorporated by reference in their entirety into this application.

STATEMENT REGARDING FEDERALLY SPONSORED RESEARCH OR DEVELOPMENT

This invention was made with government support under NIH Grant Numbers HL20558 and HL28958 awarded by the National Institutes of Health. The government has certain rights in the invention.

BACKGROUND OF THE INVENTION

Throughout this application, various publications are referenced. Full citations for these publications may be found immediately preceding the claims. The disclosures of these publications are hereby incorporated by reference into this application in order to more fully describe the state of the art as of the date of the invention described and claimed herein.

Currently, many practitioners believe that the best approach to repair of many life-threatening cardiac disorders is a cardiac transplant. Alternative approaches being tested currently are skeletal muscle myoblasts or non-transformed human mesenchymal stem cells. However, skeletal myoblasts do not become part of the cardiac synctium and few undifferentiated human mesenchymal stem cells ever become myocytes. Given the limitations in supply of hearts for transplants and the limitations in cell repair methods to date, there is a need for a more effective and generally applicable approach to cardiac repair.

SUMMARY OF THE INVENTION

This invention provides a method for treating a subject afflicted with a cardiac disorder, in vivo, comprising (i) inducing differentiation of a progenitor cell, in vitro, to a cardiogenic cell; and (ii) administering a therapeutically effective amount of the cardiogenic cell of step (i) to the subject, thereby treating the cardiac disorder in the subject.

This invention also provides a method for treating a subject afflicted with a cardiac disorder, in vivo, comprising (i) inducing differentiation of a progenitor cell, in vitro, to a cell that is destined to be cardiogenic; and (ii) administering a therapeutically effective amount of the cell of step (i) to the subject, thereby treating the cardiac disorder in the subject.

This invention further provides a method for inducing differentiation of a progenitor cell to a cardiogenic cell, in vitro, comprising forming an embryoid body cell aggregate of progenitor cells.

This invention further provides a method for determining whether a progenitor cell has differentiated to a cardiogenic cell, comprising: (a) forming an embryoid body cell aggregate of progenitor cells; and (b) determining whether a cardiac specific marker is present in a cell from the embryoid body cell aggregate of step (a), whereby the presence of a cardiac specific marker in the cell from the embryoid body cell aggregate indicates that progenitor cell has differentiated to a cardiogenic cell.

This invention further provides a method for determining whether a progenitor cell has differentiated to a cardiogenic cell, comprising: (a) determining whether a cardiac specific marker is present in progenitor cells; (b) forming an embryoid body cell aggregate of the progenitor cells of step (a); (c) determining whether the same cardiac specific marker is present in a cell from the embryoid body cell aggregate of step (b), whereby the presence of the cardiac specific marker in the cell from the embryoid cell body aggregate indicates that the progenitor cell has differentiated to a cardiogenic cell.

The invention also provides an article of manufacture comprising a packaging material having therein a cardiogenic cell differentiated from a progenitor cell.

DETAILED DESCRIPTION OF THE INVENTION

Figure 1:
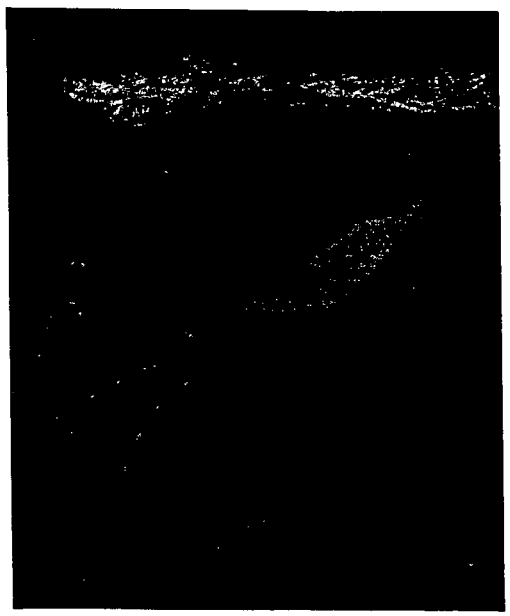
FIG. 1: Immunostaining demonstrating the co-expression of sarcomeric actinin and troponin T-C Cells were stained with primary antibodies against troponin T-C C19 (Santa Cruz SC-8121), and α-actinin, (Sigma EA-53), with donkey anti-goat Ig-G-FITC and with donkey anti-mouse IgG-TR, respectively, as secondary antibodies.
Figure 1:
Figure 1:
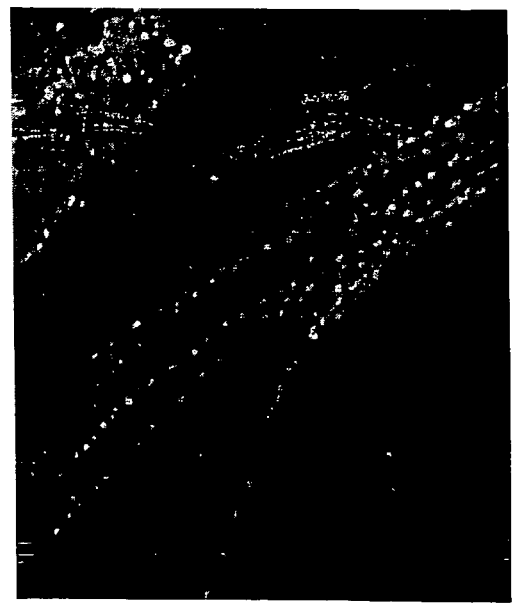
Figure 1:
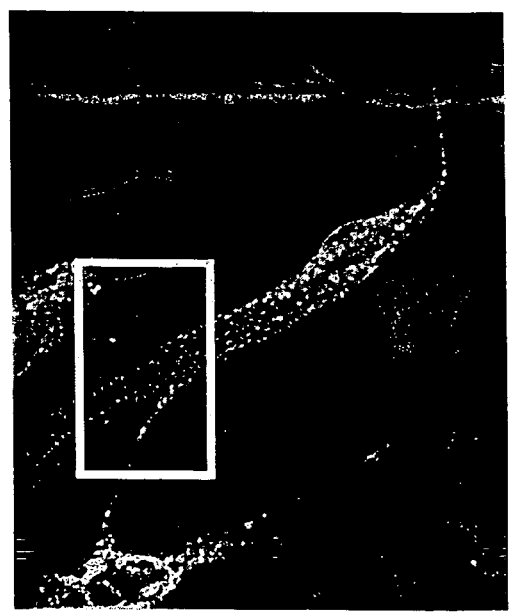

As used in this application, except as otherwise expressly provided herein, each of the following terms shall have the meaning set forth below.

As used herein, "administering" shall mean delivering in a manner which is effected or performed using any of the various methods and delivery systems known to those skilled in the art. Administering can be performed, for example, intravenously, orally, via implant, transmucosally, transdermally, intramuscularly, or subcutaneously. Specifically envisioned is topical administration. "Administering" can also be performed, for example, once, a plurality of times, and/or over one or more extended periods.

As used herein, "agent" shall include, without limitation, an organic compound, a nucleic acid, a polypeptide, a lipid, and a carbohydrate. Agents include, for example, agents which are known with respect to structure and/or function, and those which are not known with respect to structure or function.

As used herein, a "cardiogenic cell" is a progenitor cell that has been manipulated towards a cardiac lineage, but has not fully differentiated into a cardiac myocyte.

As used herein, an "embryoid body cell aggregate" is a group of cells forming a three-dimensional space, generally resulting from forces applied along multiple axes.

As used herein, "inhibiting" the onset of a disorder shall mean either lessening the likelihood of the disorder's onset, preventing the onset of the disorder entirely, or reducing or eliminating the disorder. In the preferred embodiment, inhibiting the onset of a disorder means preventing its onset entirely.

As used herein, "pharmaceutically acceptable carriers" include, but are not limited to, 0.01-0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases, and the like.

As used herein, a "progenitor cell" is a cell whose differentiation can be manipulated towards a cardiac lineage, although it has not yet fully differentiated into a cardiac cell.

As used herein, "subject" means any animal, such as a primate, mouse, rat, guinea pig or rabbit. In the preferred embodiment, the subject is a human.

As used herein, "therapeutically effective amount" means an amount sufficient to treat a subject afflicted with a disorder or a complication associated with a disorder.

As used herein, "treating" a subject afflicted with a disorder shall mean slowing, stopping or reversing the disorder's progression. In the preferred embodiment, treating a disorder means reversing the disorder's progression, ideally to the point of eliminating the disorder itself. As used herein, ameliorating a disorder and treating a disorder are equivalent.

Embodiments of the Invention

This invention provides a method for treating a subject afflicted with a cardiac disorder, in vivo, comprising (i) inducing differentiation of a progenitor cell, in vitro, to a cardiogenic cell; and (ii) administering a therapeutically effective amount of the cardiogenic cell of step (i) to the subject, thereby treating the cardiac disorder in the subject.

The subject may be a human.

The progenitor cell may be a stem cell such as a human mesenchymal stem cell or a hematopoietic stem cell. The cardiogenic cell differentiated from the progenitor cell is committed to the cardiac lineage. These cardiogenic cells are not completely differentiated to the cardiac phenotype, although they have a number of cardiac characteristics. Because these cardiogenic cells are not completely differentiated, they retain the ability to divide, which may allow them to repopulate the excised region as described in the Experimental Details section.

In an embodiment of the instant method, the differentiation of step (i) comprises forming an embryoid body cell aggregate of progenitor cells. An embryoid body cell aggregate may be formed by altering the external forces on progenitor cells to form the embryoid body or hanging progenitor cells to form the embryoid body.

In a further embodiment of the instant method, the administering of step (ii) comprises the implantation of a patch in the heart of the subject. A patch may be comprised of various materials such as a urinary bladder membrane scaffold, a natural scaffold, a synthetic scaffold, or pericardium.

In still further embodiments of the instant method, administration may comprise injection through a catheter, the use of microparticles, or direct injection through the chest wall.

Cardiac disorders treated by this method include, for example, myocardial infarction, cardiomyopathy, congestive heart failure, ventricular septal defect, atrial septal defect, congenital heart defect, ventricular aneurysm, ruptured interventricular septum, ruptured chordae tendineae, perforated mitral valve, perforated tricuspid valve, perforated aortic valve, perforated pulmonic valve, a cardiac disorder which is pediatric in origin, or a cardiac disorder which requires ventricular reconstruction.

This invention further provides a method for treating a subject afflicted with a cardiac disorder, in vivo, comprising (i) inducing differentiation of a progenitor cell, in vitro, to a cell that is destined to be cardiogenic; and (ii) administering a therapeutically effective amount of the cell of step (i) to the subject, thereby treating the cardiac disorder in the subject.

This invention further provides a method for determining whether a progenitor cell has differentiated to a cardiogenic cell, comprising: (a) forming an embryoid body cell aggregate of progenitor cells; and (b) determining whether a cardiac specific marker is present in a cell from the embryoid body cell aggregate of step (a), whereby the presence of a cardiac specific marker in the cell from the embryoid body cell aggregate indicates that the progenitor cell has differentiated to a cardiogenic cell.

Examples of cardiac specific markers include α-sarcomeric actinin, troponin, myosin heavy chain, or L-type calcium current.

This invention further provides a method for determining whether a progenitor cell has differentiated to a cardiogenic cell, comprising: (a) determining whether a cardiac specific marker is present in progenitor cells; (b) forming an embryoid body cell aggregate of the progenitor cells of step (a); (c) determining whether the same cardiac specific marker is present in a cell from the embryoid body cell aggregate of step (b), whereby the presence of the cardiac specific marker in the cell from the embryoid cell body aggregate indicates that the progenitor cell has differentiated to a cardiogenic cell.

This invention also provides an article of manufacture comprising a packaging material having therein a cardiogenic cell differentiated from a progenitor cell.

In one embodiment of this method, the article further comprises instructions for using the cardiogenic cell to treat a subject afflicted with a cardiac disorder.

Wherever applicable, the various embodiments of the instant therapeutic method are envisioned, mutatis mutandis, with respect to the instant prophylactic method and article of manufacture.

This invention is illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

Results

The formation of embryoid body (EB) cell aggregates, a known method for differentiation of embryonic stem (ES) cells in vitro, was applied to human mesenchymal stem cells (hMSCs). HMSCs were differentiated to a morphologically distinct cell type after the derivation of embryoid bodies. Embryoid bodies were grown as hanging drops in DMEM, 20% FBS for 3 days.

HMSCs were cultured in MSC growing medium at 37° C. in a humidified atmosphere of 5% $CO_2$. Cells were used from passages 2 to 4. For induction of differentiation, EBs were formed in hanging drops of 25,000 cells in 20 μl of DMEM supplemented with 20% FBS. After 3 days, EB were plated on culture dishes and cultivated for additional 5-13 days.

Using hMSCs stably or transiently transfected with cardiac-specific α-cardiac myosin heavy chain (MHC) promoter-driven enhanced green fluorescent protein (EGFP) it was shown that the EB formation markedly increased the number of EGFP-positive cells. A cardiac precursor population—cells expressing EGFP—were observed within hMSC derived embryoid bodies cultured in DMEM, 20% FBS, 3-5 days after derivation. When plated and maintained in adherent culture, EB cells proliferated.

Immunostaining demonstrated the co-expression of alpha sarcomeric actinin and troponinT-C, markers for cardiac muscle cells (see FIG. 1). Cells were stained with the primary antibody against troponinT-C C19 (Santa Cruz SC-8121), and α-actinin, (Sigma EA-53), with donkey anti-goat Ig-G-FITC and with donkey anti-mouse IgG-TR, respectively, as secondary antibodies.

Figure 2:
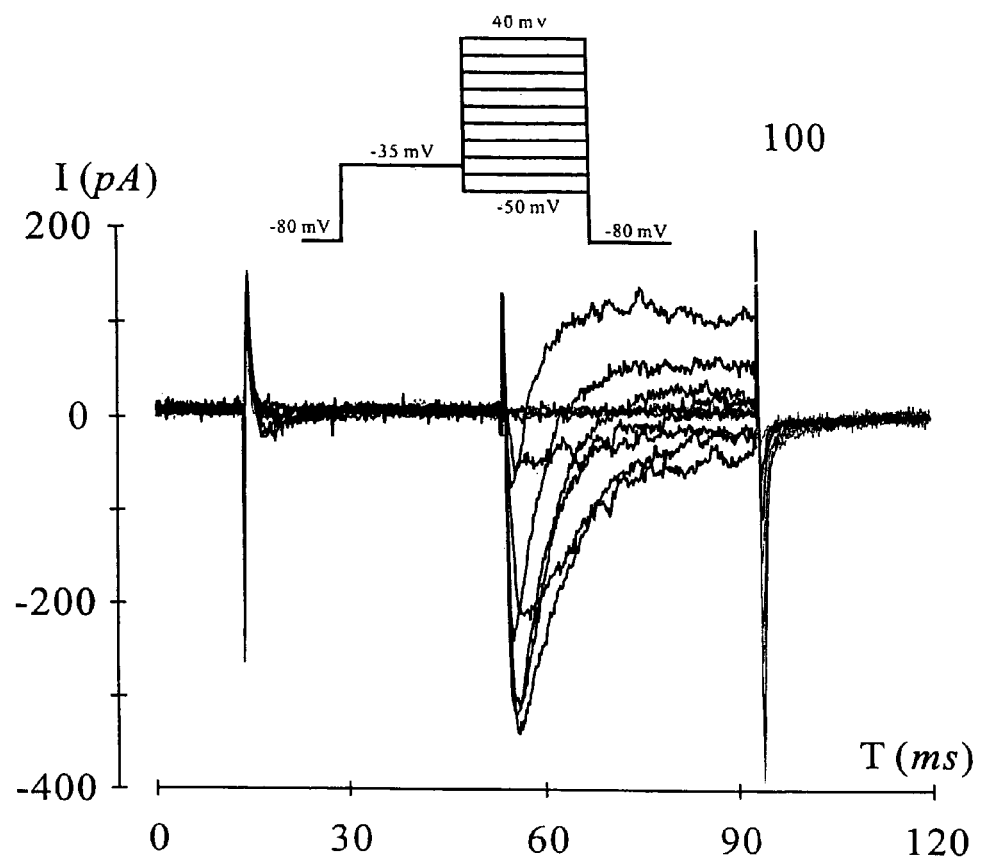
FIG. 2: Human mesenchymal stem cells expressing voltage dependent L-type $Ca2+$ channels under cardiac differentiation The figure inset at the top shows the experimental protocol. The cell from the cardiogenic cell line was held at −80 mV and depolarized to −35 mV where a small inward current was observed. A second step from −35 mV revealed an appreciable L-type calcium current. The lower portion of the figure shows the right half of the upper protocol and the corresponding peak inward current-voltage relationship. The peak inward current occurs at 0 mV again consistent with L-type calcium current as its origin.
Figure 2:
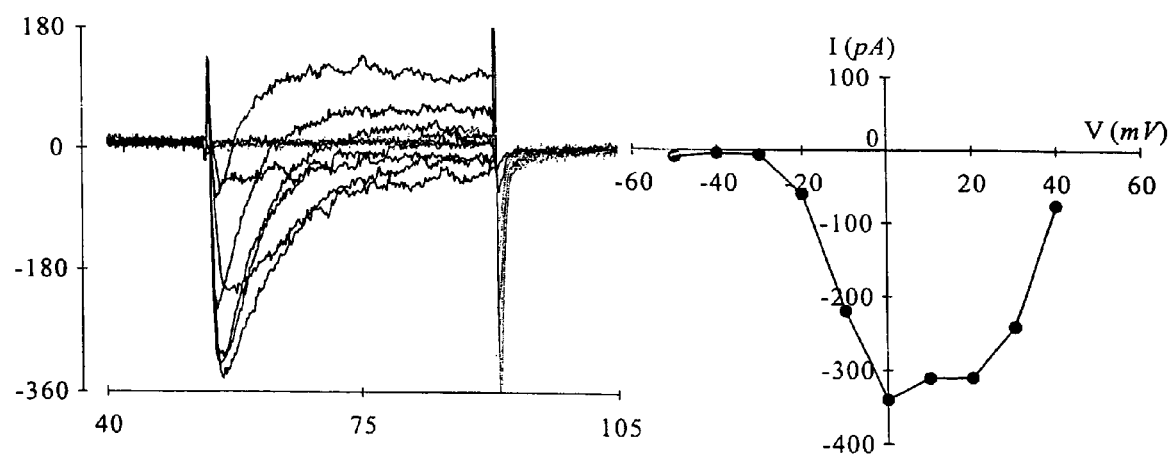

HMSCs-derived cardiac precursors also exhibited a functional phenotype of early-stage cardiomyocytes, that is, electrical activity. At day 13 after plating EB cells, the noncontracting precursor cells formed from stably transfected hMSCs were green and displayed voltage-dependant L-type $Ca^{2+}$ channels (see FIG. 2). The figure inset at the top shows the experimental protocol. The cell from the cardiogenic cell line was held at −80 mV and depolarized to −35 mV where a small inward current was observed. A second step from −35 mV revealed an appreciable L-type calcium current. The lower portion of the figure shows the right half of the upper protocol and the corresponding peak inward current-voltage relationship. The peak inward current occurs at 0 mV again consistent with L-type calcium current as its origin. Undifferentiated hMSCs did not have this current under these recording conditions (data not shown). This novel directed differentiation approach led to the efficient derivation of cardiac precursor cells from hMSCs.

To test the ability of the cardiogenic cells to perform useful mechanical work in the heart, a full thickness defect was created in the right ventricle of dogs. Patches seeded with the cardiogenic cells were implanted and assessed 8 weeks later. For comparison, the following groups were also studied: baseline (no surgery); patch alone, and Dacron patch (current standard of care). The cardiogenic cell seeded patches produced the most regional work of all patch implanted groups, nearly doubling that of the second highest patch. Below are details of the procedures.

All animals received humane care in compliance with the "Principles of Laboratory Animal Care" formulated by the National Society for Medical Research and the "Guide for the Care and Use of Laboratory Animals" prepared by the National Academy of Sciences and published by the National Institutes of Health (NIH Publication No. 85-23, revised 1985). In addition, the Institutional Animal Care and Use Committee at SUNY Stony Brook reviewed and approved the protocol (IACUC # 20031326).

Initial Surgery

Adult mongrel dogs (20-30 kilograms) were sedated with ketamine, intubated, and placed under general anesthesia (isoflurane). The right chest and groin were prepped and draped in the normal sterile fashion. A right femoral arterial line was placed percutaneously. The right chest was opened using a right anteromedial incision over the fifth intercostal space. A pericardial cradle was constructed. A 3-0 silk stitch was placed into the right ventricle (RV) and pulled upward. A portion of the posterolateral right ventricular free wall was isolated using a Satinsky clamp in an oblique fashion. Hemodynamic stability was confirmed by continuous arterial pressure monitoring. A full thickness portion of myocardium, approximately 15×10 mm, was excised. To test the adequacy of the defect, a suture was placed above and below its long axis, and the Satinsky clamp was slowly released. If a full thickness defect was not seen, the myocardium was re-excised. A myocardial patch (Table 1) was used to repair the defect with a running 5-0 prolene suture. The clamp was released. Pulsatile defects were repaired by placing additional single interrupted 5-0 prolene suture. A chest tube was placed to evacuate residual pneumothorax. Once adequate hemostasis was obtained, the chest was closed in the standard fashion.

Terminal Surgery

Eight weeks later, the animal was returned to the operating room, sedated with ketamine, intubated and placed under general anesthesia (isoflurane). The animal was placed in the supine position. A catheter was placed in the femoral artery for hemodynamic monitoring. The anterior chest wall was removed via bilateral thoracotomy and the mediastium was exposed. Adhesions were carefully dissected off the heart to expose the patch and its suture line. A pressure transducer (Millar Instruments) was placed into the RV.

Measurement of Regional Systolic Function

Regional function was determined by high density mapping (HDM) (Kelly, Azeloglu et al. 2004). A region of interest (ROI) was selected on the myocardial patch, and covered with speckles composed of silicon carbide particles that created a random high contrast light intensity distribution used to measure epicardial surface deformation. Next, a complimentary metal-oxide semiconductor (CMOS) camera (Photron) was focused on the ROI, and images were taken at 250 frames per second. Using a subpixel extended phase correlation algorithm (Foroosh, Zerubia et al. 2002), high-resolution displacement maps were obtained. These data were used to calculate area change in the ROI. Regional stroke work (RSW) was calculated by integrating RV pressure with respect to area (normalized to developed pressure and end diastolic regional area). Systolic area contraction (SAC) was defined as the end diastolic area minus the end systolic area (normalized to the end diastolic area). Baseline data from non-operated dogs were obtained from approximately the same anatomic location.

Histology

Specimens of the patch area in all groups were placed in 4% paraformaldehyde and later transferred to 30% sucrose solution. The specimens were then placed in an embedding matrix and sectioned at a thickness of 10 microns. These sections were stained with hematoxylin and eosin (H&E) and alpha sarcomeric actinin.

For actinin staining, each slide was soaked for 15 minutes in PBS buffer and cells were permeabilized with 0.2% Triton X-100 in PBS for 5 minutes, and then blocked with 5% normal goat serum in PBS. The section was then incubated with alpha sarcomeric actinin antibodies (clone EA-53, Sigma) and stained with fluorescein isothiocyanate (FITC)

conjugated goat anti-mouse antibodies (Santa Cruz Biotechnology). The nuclei were counterstained with DAPI (Molecular Probes) and slides were mounted on coverslips with Vectashield mounting media (Vector Laboratories). Immunofluorescence was analyzed by deconvolution microscopy using the AxioVision 4.1 imaging software package (Carl Zeiss) coupled with an Axiovert 200M fluorescence microscope (Carl Zeiss). Cross-sectional images were obtained with 250-nm Z-stack steps and processed using the AxioVision 4.1 constrained iterative algorithm.

Experimental Groups

To assess the ability of the cardiogenic cells to differentiate into cardiac myocytes after implantation in the heart, the cells were seeded on to a urinary bladder membrane (UBM) scaffold. As the UBM scaffold alone may be able to attract myocytes, the UBM was implanted scaffold without any cells seeded on it. Currently, use of a Dacron patch is the standard of care for replacing infarcted myocardium. Therefore, dogs implanted with a Dacron myocardial patch were also tested. To establish baseline function, a separate group of animals was used. The baseline animals were not subjected to patch implantation surgery, and were only operated on for the acquisition of data in the terminal phase of the experiment. The groups examined are summarized in Table 1.

Microscopic Results

The Dacron group displayed fibroblast proliferation with abundant collagen deposition organized in a dense manner. The Dacron patch was intact; there was no infiltration by cellular elements. Cardiomyocytes were not evident on the Dacron patch. In the UBM patch region, clusters of cardiomyocytes, which stained positive for alpha sarcomeric actinin, were seen along the endocardial surface. The region of the cardiogenic cell seeded patch was composed of multiple areas, located throughout, that stained positive for GFP and alpha sarcomeric actinin.

Regional Systolic Function

Figures 3A, 3B, 3C:
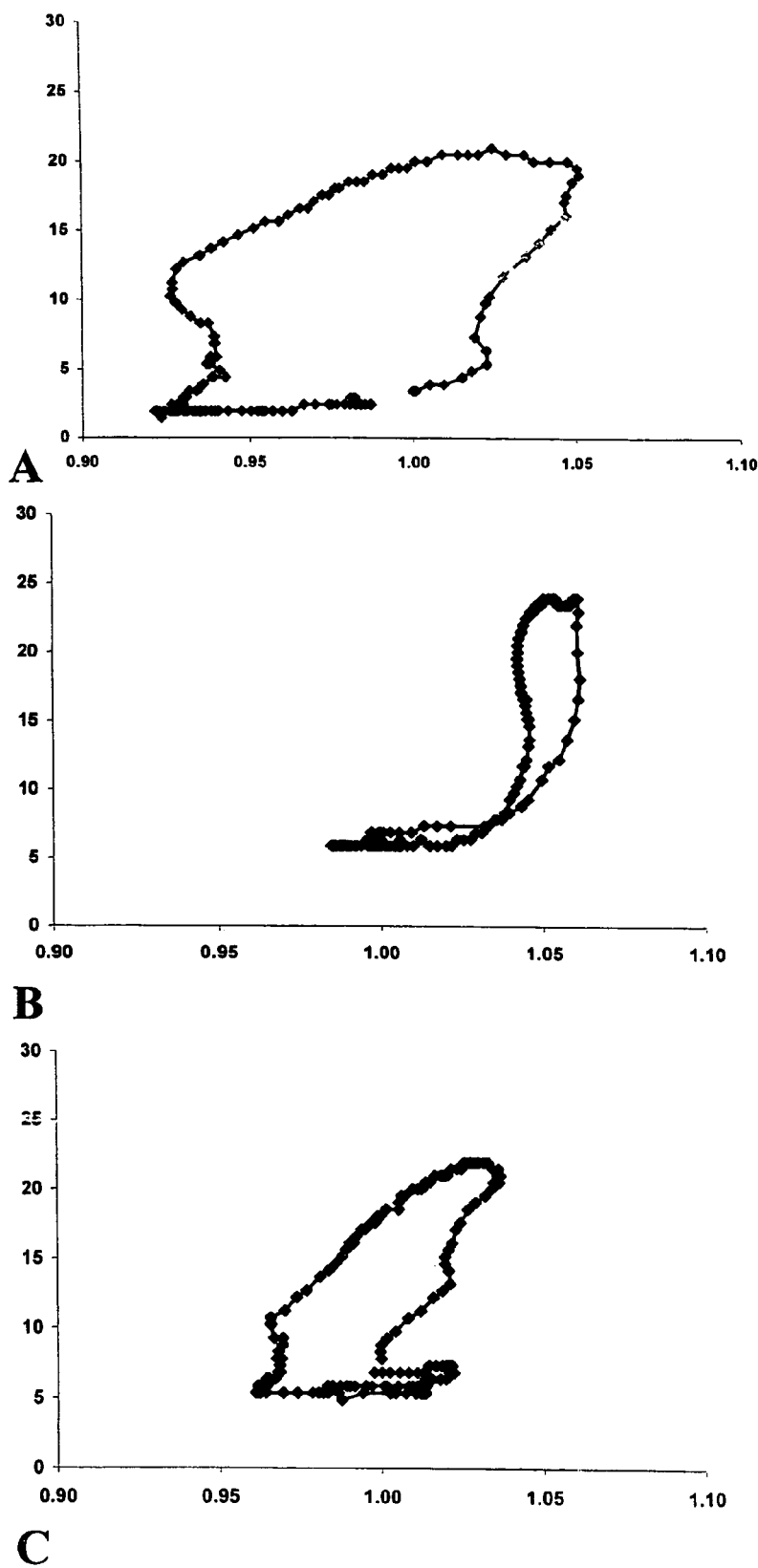
FIGS. 3A-3C: Examples of regional work loops A regional work loop from a cardiogenic seeded patch is shown as FIG. 3A. A regional work loop from a Dacron patch is shown as FIG. 3B. A regional work loop from an unseeded UBM patch is shown as FIG. 3C.
Figure 4:
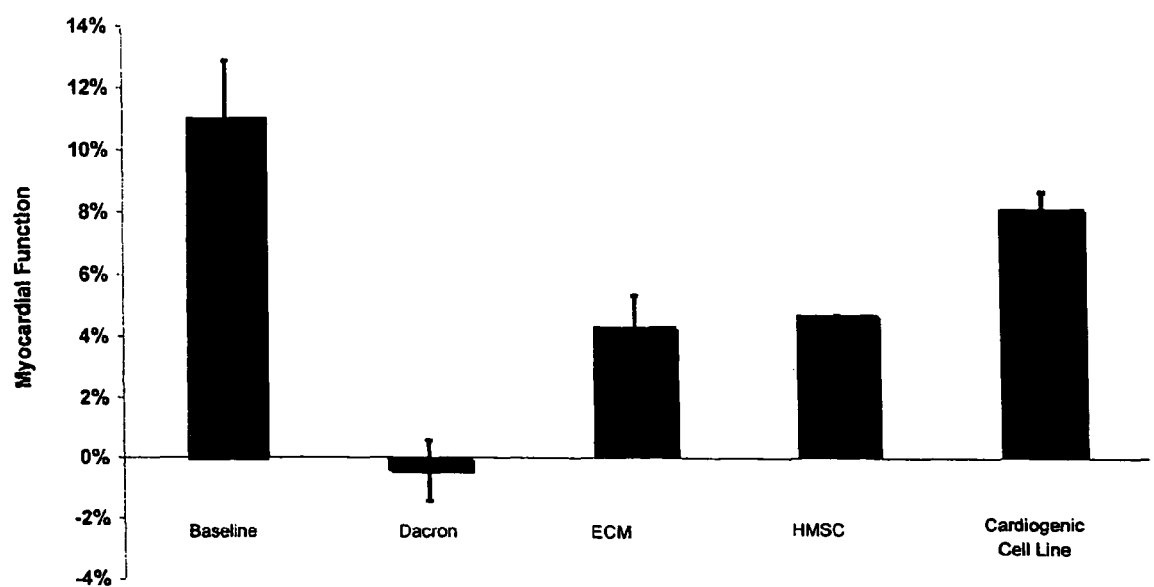
FIG. 4: Cardiogenic cells as compared to alternatives including human mesenchymal stem cells Patches seeded with cardiogenic cells were compared with a patch seeded with hMSCs. The regional stroke work (RSW) in the hMSC heart was 4.7%, compared to 8.2% in hearts implanted with cardiogenic cell seeded patches. These data demonstrate that the cardiogenic cell line generates the most myocardial function of all alternatives tested, and also demonstrates specifically that the cardiogenic cell line is superior to hMSCs not committed to a cardiac lineage.

Examples of regional work loops are shown in FIG. 3. Average RSW in baseline was 12.8±0.7. The Dacron patch performed no regional work (RSW=−0.4±1.0). RSW in the un-seeded UBM patch region was 4.3±1.0. However, in the cardiogenic seeded patch, regional stroke work (RSW=8.2±0.5) increased by 90% compared to un-seeded UBM patches, and 75% compared to the hMSC seeded patch.

Similar improvements were also noted in the cardiogenic cell seeded patch region in terms of systolic area contraction (SAC). The cardiogenic cell seeded patch demonstrated a SAC of 10.3%, an increase of 220% compared to the un-seeded UBM patch (SAC=3.2%) or an increase of 87% compared with a patch seeded with hMSCs (SAC=5.5%).

Conclusion

Cardiogenic stem cells and their progeny are viable for at least 8 weeks after implantation in the beating heart. The presence of cardiogenic stem cells correlates with improved regional function, which is greater than an acellular scaffold alone, an acellular scaffold seeded with hMSCs, or a Dacron patch.

TABLE 1

| Experimental Groups Studied |
| --- |
| 1. Cardiogenic seeded UBM |
| 2. UBM (no cells seeded) |
| 3. hMSC seeded UBM |
| 4. Dacron |
| 5. Baseline |

References

Foroosh, H., J. B. Zerubia, et al. (2002). "Extension of phase correlation to subpixel registration." *IEEE Transactions on Image Processing* 11(3): 188-200.

Kelly, D., E. Azeloglu, et al. (2004). "Accuracy and reproducibility of a subpixel extended phase correlation method to determine micron level displacements in the heart." *Medical Engineering & Physics*: Submitted.

What is claimed is:

1. A method for treating a subject afflicted with a cardiac disorder associated with a loss of cardiac myocytes, in vivo, comprising:
    (i) inducing differentiation of human mesenchymal stem cells, in vitro, into cardiogenic cells by forming an embryoid body of the mesenchymal stem cells;
    (ii) expanding the cardiogenic cells of step (i) in culture in culture medium comprising serum without additional cardiac myocyte differentiation factors,
    (iii) administering a therapeutically effective amount of the cardiogenic cells of step (i) to the subject, thereby treating the cardiac disorder in the subject.

2. The method of claim 1, wherein the subject is a human.

3. The method of claim 1, wherein forming an embryoid body comprises altering the external forces on the mesenchymal stem cells to form the embryoid body or hanging the mesenchymal stem cells to form the embryoid body cell aggregate.

4. The method of claim 1, wherein the administering of step (iii) comprises implanting a patch in the heart of the subject, injection through a catheter, use of microparticles, systemic administration or direct injection through the chest wall.

5. The method of claim 4, wherein the patch is comprised of a urinary bladder membrane scaffold, natural or synthetic scaffold, or pericardium.

6. The method of claim 1, wherein the cardiac disorder is myocardial infarction, cardiomyopathy, congestive heart failure, ventricular septal defect, atrial septal defect, congenital heart defect, ventricular aneurysm, a cardiac disorder which is pediatric in origin, ventricular aneurysm, or a cardiac disorder which requires ventricular reconstruction.

7. A method for inducing differentiation of human mesenchymal stem cells, in vitro, to cardiogenic cells comprising forming an embryoid body of the mesenchymal stem cells thereby inducing the mesenchymal stem cells to differentiate into cardiogenic cells.

8. The method of claim 7, wherein the step of forming an embryoid body comprises altering the external forces on the mesenchymal stem cells to form the embryoid body, or hanging the mesenchymal stem cells to form an embryoid body.

9. Cardiogenic cells made by forming an embryoid body in vitro of mesenchymal stem cells thereby inducing the mesenchymal stem cells to differentiate into cardiogenic cells.

10. The cells of claim 9, wherein the cardiogenic cells and mesenchymal stem cells are human cells.

* * * * *

UNITED STATES PATENT AND TRADEMARK OFFICE
CERTIFICATE OF CORRECTION

| | | |
|---|---|---|
| PATENT NO. | : 8,431,397 B2 | Page 1 of 1 |
| APPLICATION NO. | : 11/227533 | |
| DATED | : April 30, 2013 | |
| INVENTOR(S) | : Robinson et al. | |

It is certified that error appears in the above-identified patent and that said Letters Patent is hereby corrected as shown below:

On the title page item (73), in addition to Assignee: The Trustees of Columbia University in the City of New York, New York, NY (US), the patent should also include Assignee: The Research Foundation of State University of New York, Albany, NY (US).

Signed and Sealed this
Sixteenth Day of June, 2015

Michelle K. Lee
*Director of the United States Patent and Trademark Office*